US007763175B2

(12) United States Patent
DeCoster et al.

(10) Patent No.: US 7,763,175 B2
(45) Date of Patent: Jul. 27, 2010

(54) ELECTROMAGNETIC PROBE DEVICE

(75) Inventors: Mark A. DeCoster, Covington, LA (US); Nicolas G. Bazan, New Orleans, LA (US)

(73) Assignee: The Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1325 days.

(21) Appl. No.: 11/130,971

(22) Filed: May 17, 2005

(65) Prior Publication Data

US 2006/0263890 A1 Nov. 23, 2006

(51) Int. Cl.
*B01D 35/06* (2006.01)
*G01N 33/553* (2006.01)

(52) U.S. Cl. ........................ 210/695; 210/222; 436/526

(58) Field of Classification Search ................. 210/222, 210/223, 695; 436/526
See application file for complete search history.

(56) References Cited

U.S. PATENT DOCUMENTS

2002/0182751 A1* 12/2002 Herr et al. .................. 210/695
2004/0021073 A1 2/2004 Barbic et al.

OTHER PUBLICATIONS

Matthews, B.D., et al, "Mechanical Properties of Individual Focal Adhesions Probed With a Magnetic Microneedle," Biochem Biophys Res Commun. Jan. 16, 2004;313(3);758-64.

* cited by examiner

*Primary Examiner*—David A Reifsnyder
(74) *Attorney, Agent, or Firm*—Jason P. Mueller; Adams & Reese LLP

(57) ABSTRACT

The invention is an electromagnetic probe used in conjunction with a ferrofluid containng M particles. The electromagnetic probe is used to steer M-particles to a desired location, or use the M particles for mixing the ferrofluid. The probe can be used in conjunction with a microscope, a micromanipulator, a catheter or endoscope.

13 Claims, 10 Drawing Sheets

ELECTROMAGNETIC PROBE DEVICE

FIELD OF INVENTION

The invention relates to a portable electromagnetic probe that is used with ferrofluids in a in a variety of applications, including particle separation, particle placement and particle delivery, and particle mixing.

BACKGROUND OF THE INVENTION

Magnetic separation is a recent simple technique for isolation of cells, particles and organic molecules from complex mixtures by association, conjugating or labeling the molecule desired with a magnetic responsive material. The magnetic responsive material can be microbeads, such as the superparamagnetic beads available from Dynal Biotech as Dynabeads, magnetic nanoparticles, such as StemSep available from StemCell Technologies, and other magnetic particles or molecules that can be combined or attached to the cell or organic molecule of interest. Such magnetically "labeled" organic material is then positioned within a magnetic field to effect separation of the labeled material. The advantage of magnetic separation is that the process is gentle, and hence does not present the potential physical and/or chemical damage that may result with centrifuge separation methods. Selection can be positive (to isolate and retain the magnetic labeled particles) or negative (to remove or exclude the magnetic labeled particles)

Magnetism can also be used to stir or mix materials. However, in prior art magnetic separation/stirring technologies, fixed bulky bar magnets are used. For instance, prior art magnetic separators employ bar magnets. The sample containing the labeled magnetic material is positioned adjacent to the magnet, and left for a period of time to allow labeled particles to migrate to the magnet under the influence of the magnetic force. A magnetic separator manufactured by Dynal Biotech employed a single bar magnet and the samples are placed adjacent to the magnet for separation. Another magnetic separator manufactured by Invitrogen (the Captivate Microscope Mounted Magnetic Yoke) uses two bar magnets mounted horizontally side by side with a center horizontal channel between the magnets. A sample containing a ferrofluid is positioned in the channel, where separation occurs though the magnetic forces exerted by the bar magnets. The yoke is designed to be inserted into a compound microscope where the process can be monitored. Another magnetic separator available from Miltenyi Biotec is similar, but uses a vertical yoke having two bar magnets positioned vertically side by side with a channel or column positioned there between. The material is flowed into the column, where separation occurs.

Prior art magnetic mixers or stirrers generally utilize a mixing agitator or paddle positioned within a container. The paddle is rotated within the container through the use of externally generated magnetic fields, such as created by externally rotating magnets, such as taught in U.S. Pat. Nos. 5,478,148; 5,586,823 and 6,383,827. These prior art magnetic mixing tools are cumbersome and the strength of the magnetic field is difficult to modify and control without replacing the magnets. There is no ability to vary the application of the magnetic force spatially. These tools lack compactness and could not be used to move ferrofluids in vivo (for purposes of this application, a ferrofluid is a flowable substance where a portion of the substance is responsive to a magnetic field). Materials that are responsive to a magnetic field are referred to as M particles. Hence, a portion of a ferrofluid must consist of M particles. The ferrofluid may have nanoscale or micrometer sized M particles suspended in a carrier fluid, or cells incorporating a magnetically responsive material suspended in a carrier fluid. M particles, if contained in a carrier, may appear as a solid or a liquid if separated from the carrier.

SUMMARY OF THE INVENTION

The Invention includes a portable electromagnetic probe having a core and windings powered generally by DC current. The probe is used in conjunction with a ferrofluid to guide the M particles contained in the ferrofluid to a desired location. The probe may be used in conjunction with a microscope, endoscope, or catheter.

OBJECTS OF THE INVENTION

It is an object of the invention to use a portable electromagnetic probe to steer M particles in a ferrofluid.

It is an object of the invention to incorporate an electromagnetic probe into an endoscope or catheter type device.

It is an object of the invention to use an electromagnetic probe with M-particles as a mixing device.

It is an object of the invention to use an electromagnetic probe to separate samples.

DETAILED DESCRIPTION OF THE PREFERRED EMBODIMENT

Figure 1:
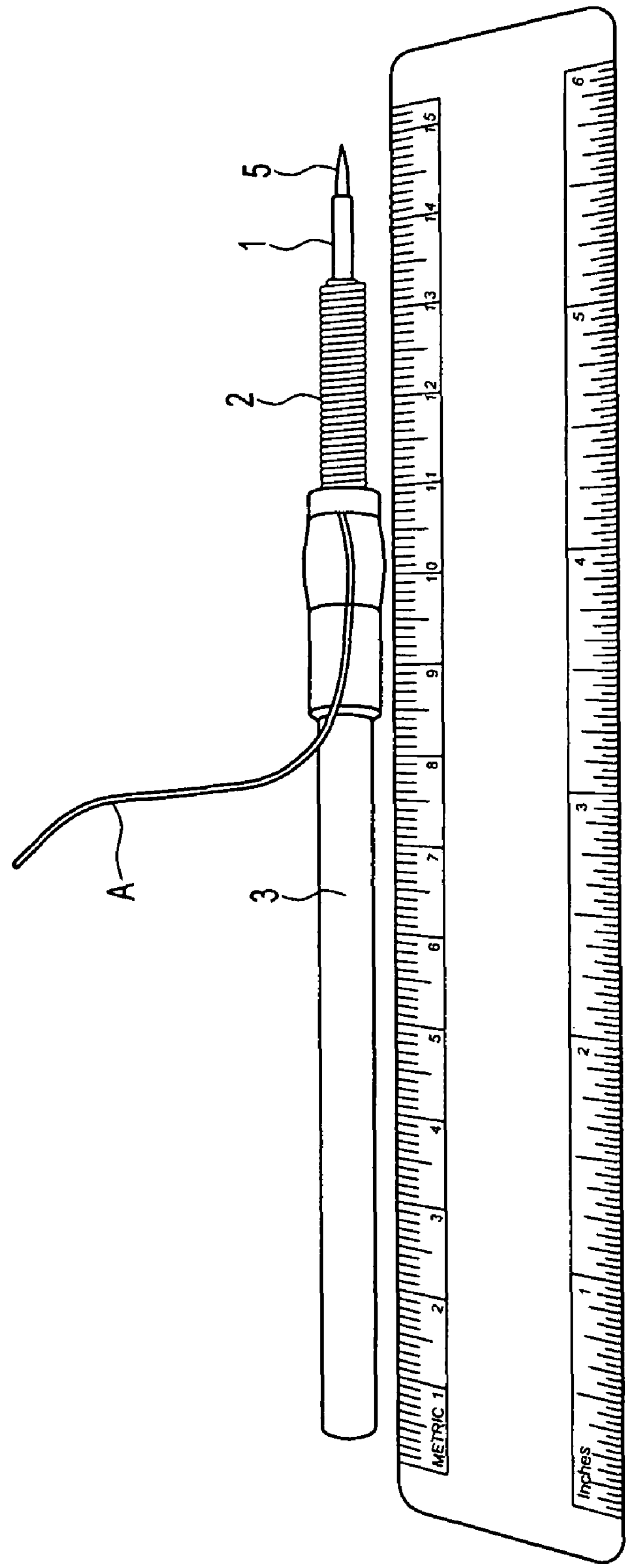
FIG. 1 show a stylus style electromagnetic probe.

Shown in FIG. 1 is a prototype stylus style electromagnet probe suitable for use with a microscope, such as by attaching the probe to a micromanipulator. The probe A has a core 1, and conductive windings 2 surrounding the core 1. The windings are electrically connected to a DC power source. As shown, the core 2 is generally cylindrically shaped and has one end, the probe end 5, which is preferably pointed. The pointed probe end allows for accurate visualization of the placement of the electromagnetic probe and channeling of the magnetic field around the axis of the probe tip. In the prototype, the core was a steel dissection pin (about 1/16 inch in diameter) and the windings are copper wire. As shown in FIG. 1, the probe A includes cylindrical body 3 on which the core and windings are mounted to create a stylus electromagnetic probe. The prototype stylus probe is about six inches long, with a core diameter of about a sixteenth of an inch and the core/windings diameter of about ¼ inch. The windings terminal ends are connected to a variable DC power source (available from Jameco Electronics). In one embodiment, the power supply was capable of producing up to nine amps of power. The prototype probe produced about 40 Gauss magnetic field (as measured near the probe end) when connected to this power source.

Figure 2:
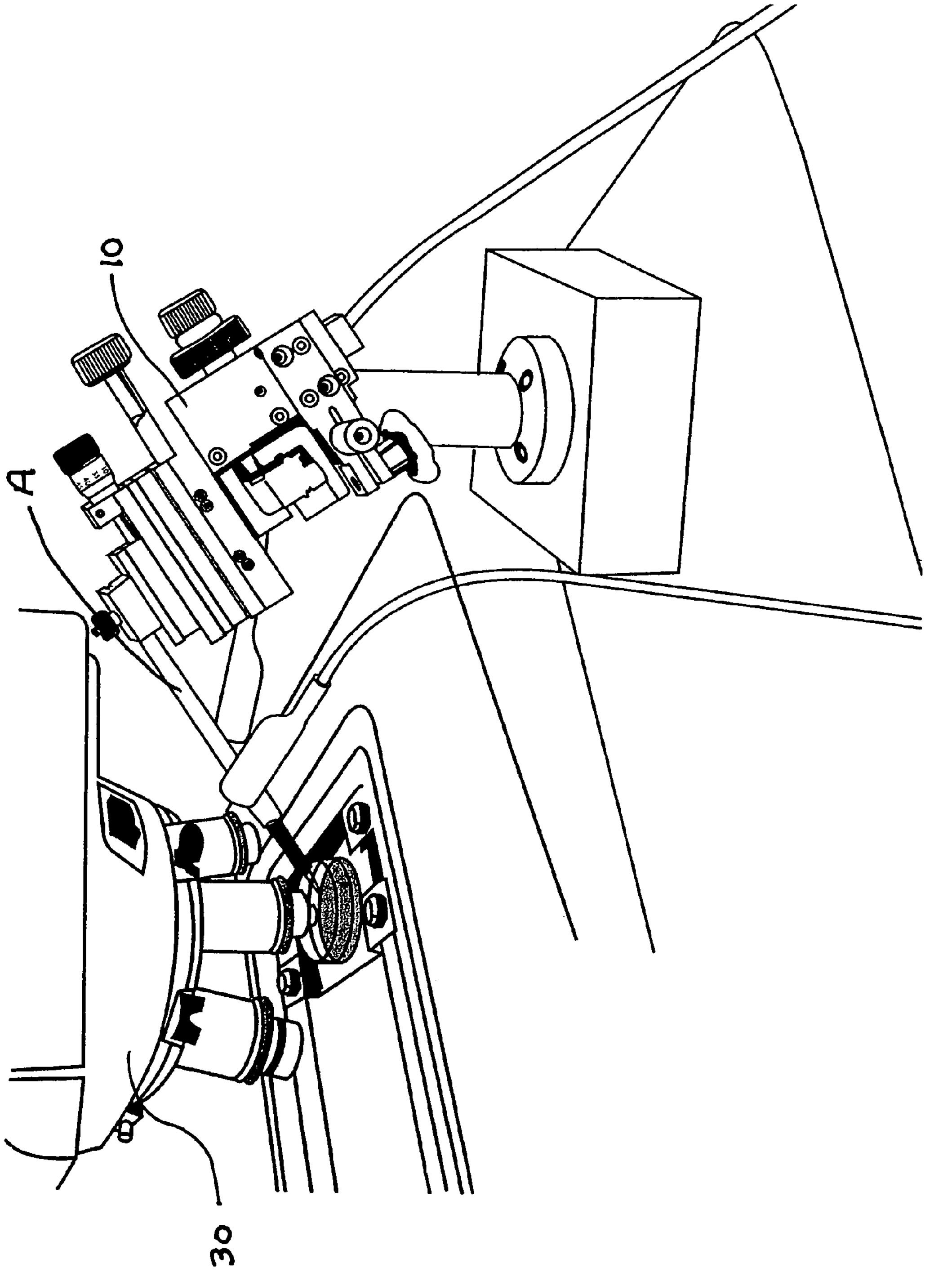
FIG. 2 shows the stylus probe used with an upright microscope
Figure 3:
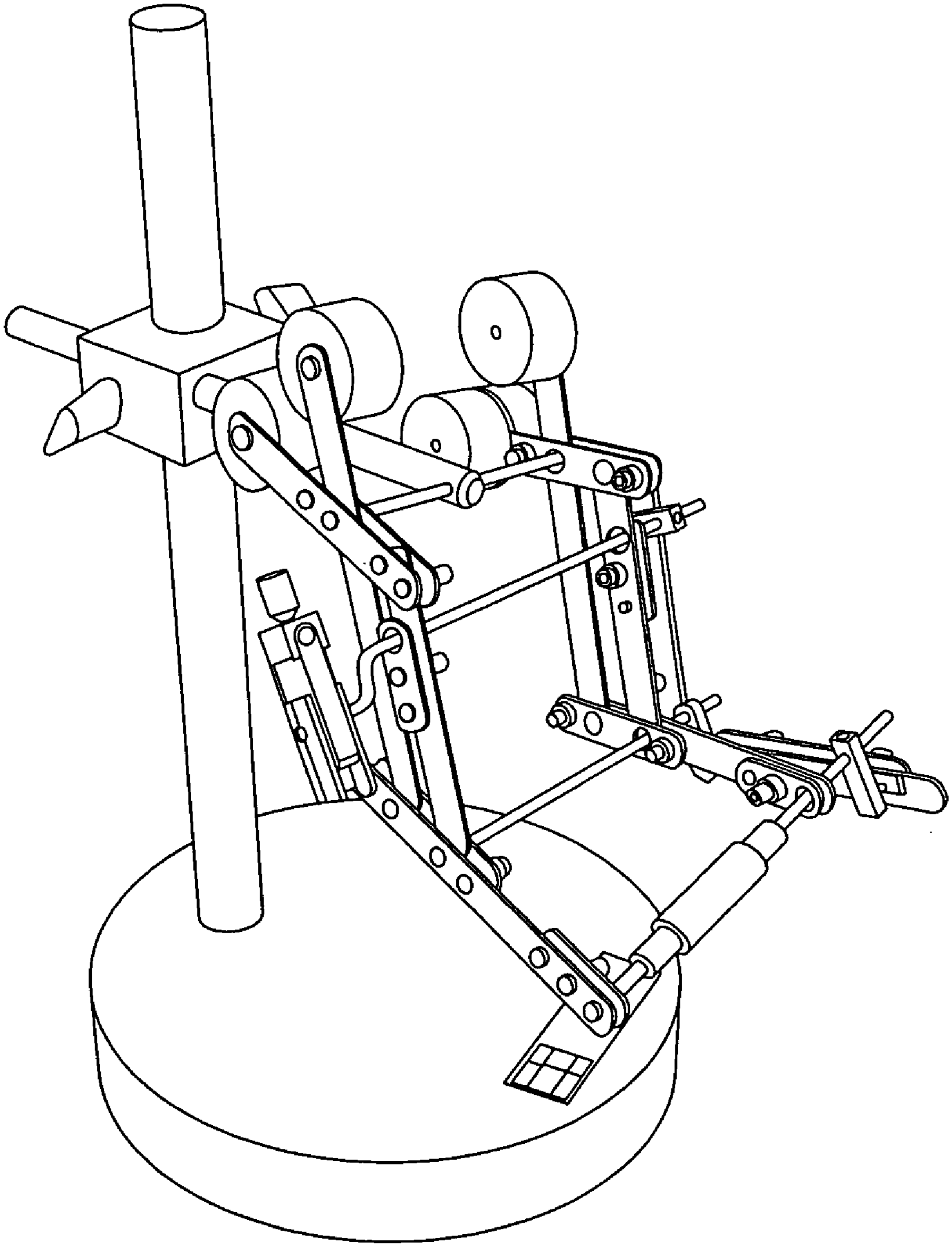
FIG. 3 shows a pantograph type micromanipulator.
Figure 4:
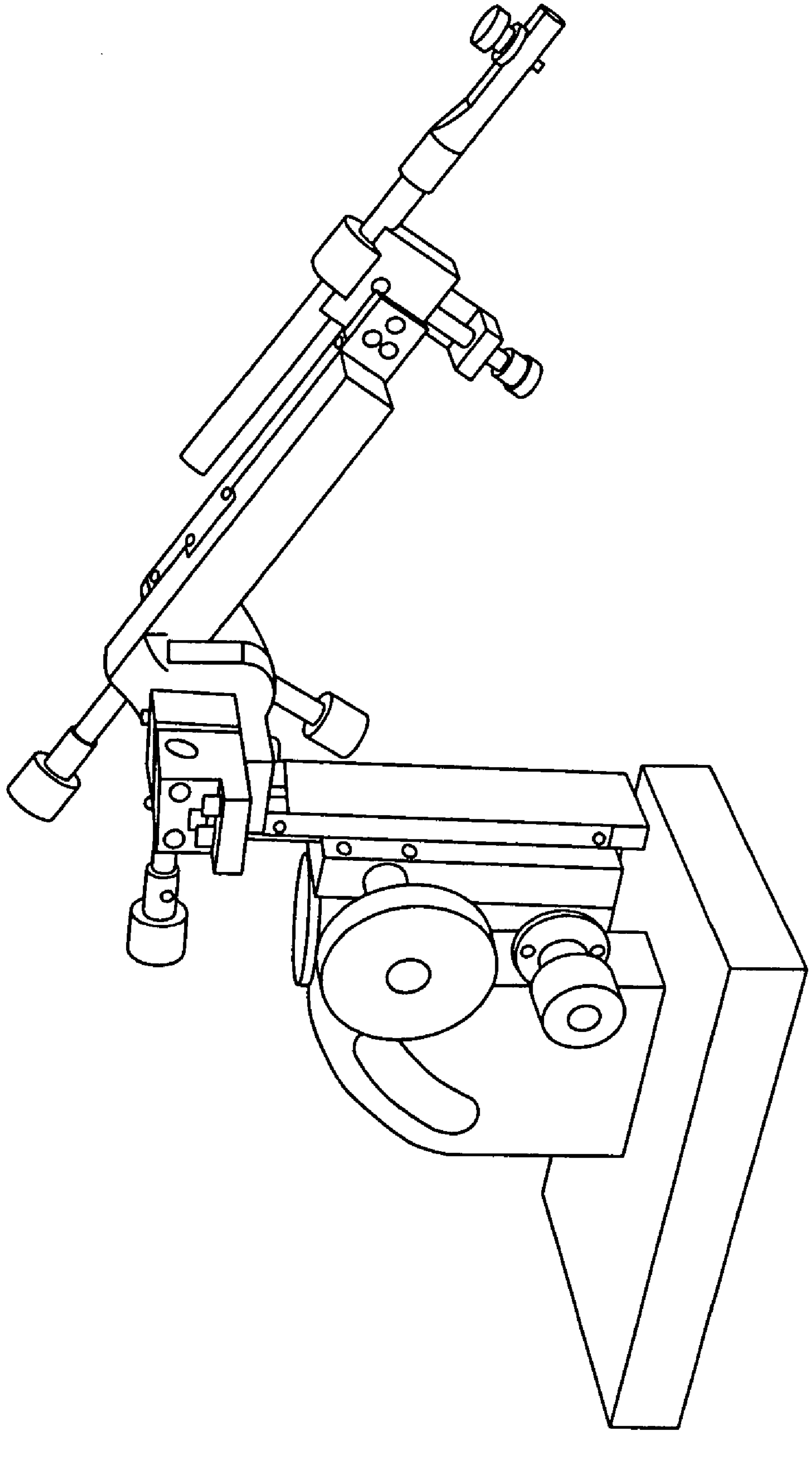
FIG. 4 shows another embodiment of a prior art micromanipulator
Figure 5A:
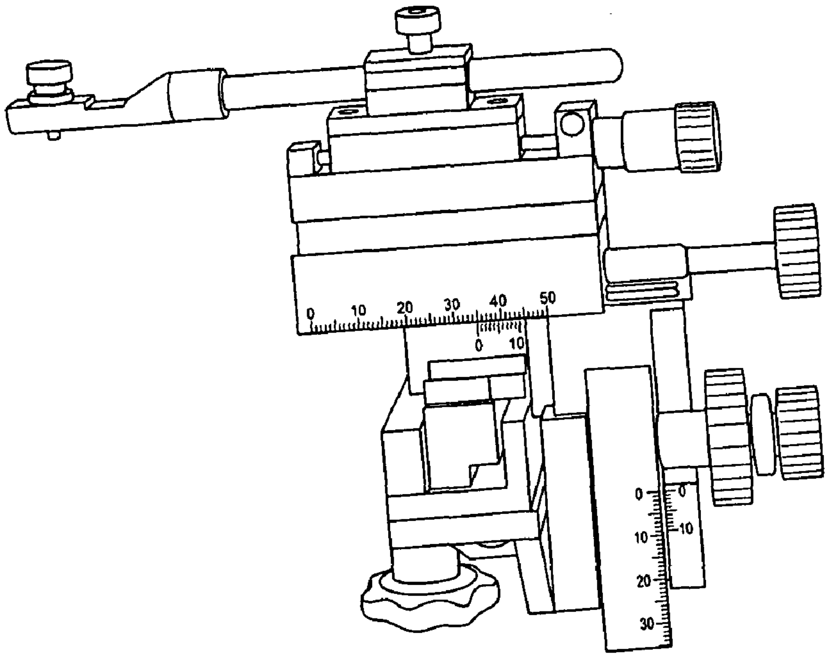
FIG. 5 shows a roller bearing type micromanipulator
Figure 5B:
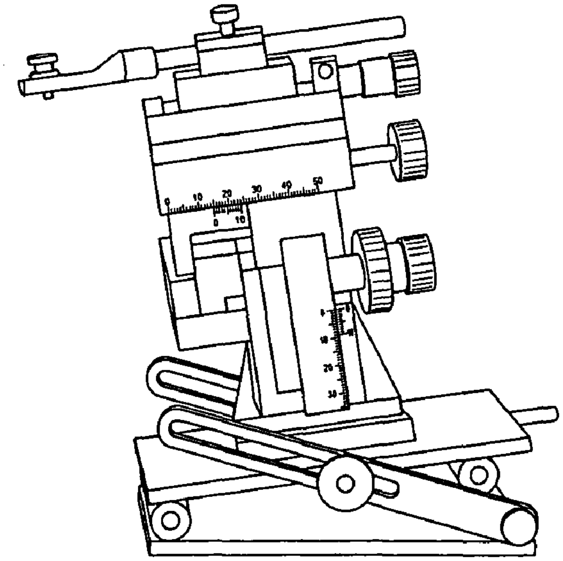
Figure 6:
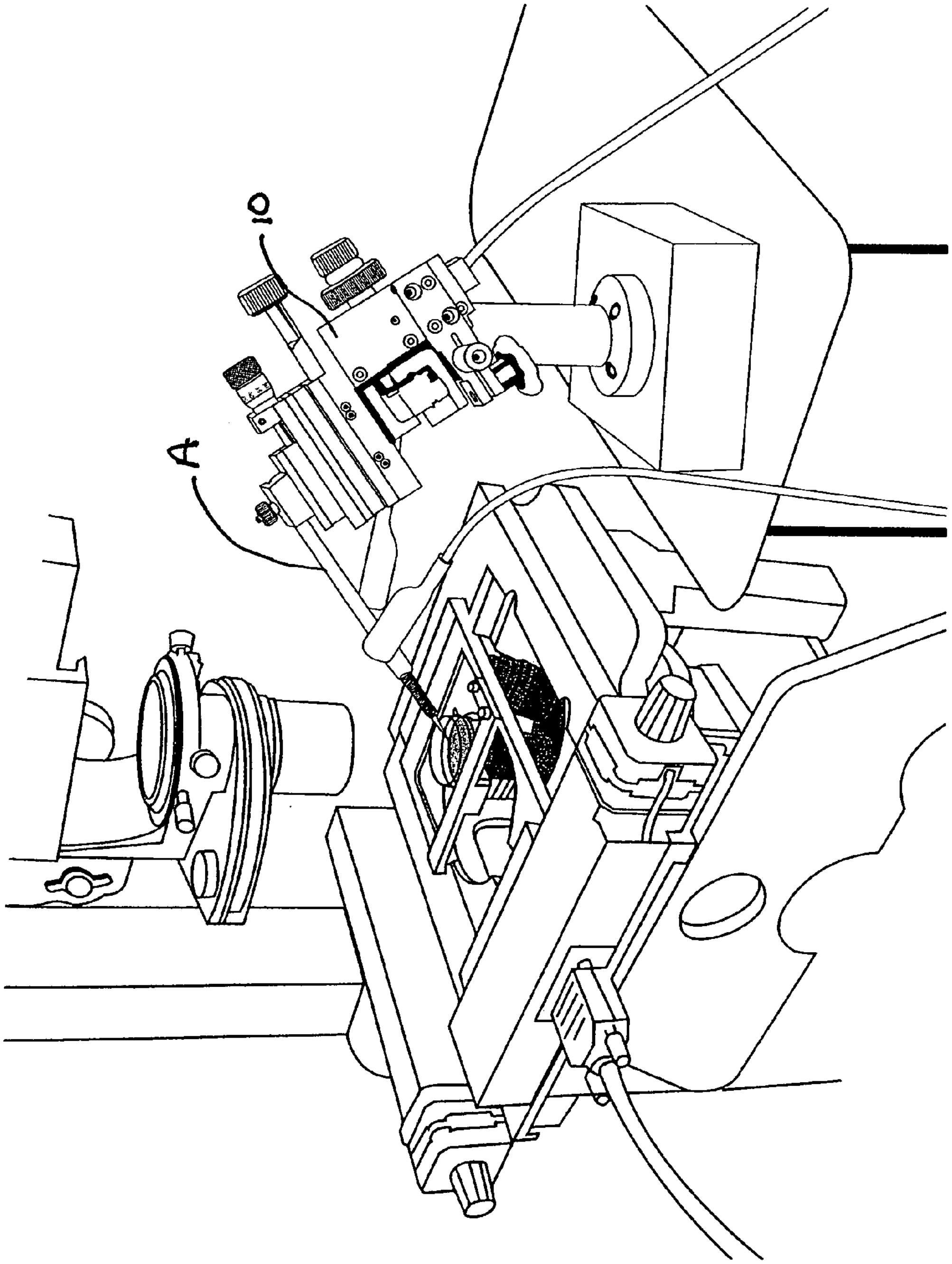
FIG. 6 shows the stylus style probe used with an inverted microscope.

Shown in FIG. 2 is the stylus probe used in conjunction with an upright microscope 30. The probe A is mounted in a micromanipulator 10. The micromanipulator 10 allows for independent positioning of the x-y-z axis, and hence allows for accurate placement of the probe tip when mounted in the micromanipulator arm. FIGS. 3-5 show various commercially available micromanipulators: FIG. 3 shows a pantograph type manipulator; FIG. 4 is a dovetail slide manipulator; and FIG. 5 shows a roller bearing type manipulator, all available from Stoelting Co. of Wood Dale Il. Other types of manipulators are commercially available. Each manipulator has a carrier for holding or clamping a tool (or a carrier that can be attached to the manipulator, such as a microgripper), and one of more controls that operate to vary the x-y-z location of the carrier, and hence the "carried" tool. Micromanipulator tools can be hydraulically activated, mechanically activated, and manually operated or remotely operated. Micromanipulators can be clamped or otherwise attached to the microscope or positioned on an independent manipulator base. The probe can easily be used in conjunction with an inverted, upright or confocal microscope; for instance, shown in FIG. 6 is the stylus probe A used in conjunction with an inverted microscope. The stylus probe is positioned to allow interaction of the probe's magnetic fields with a sample positioned on the stage of the microscope.

Figure 7A:
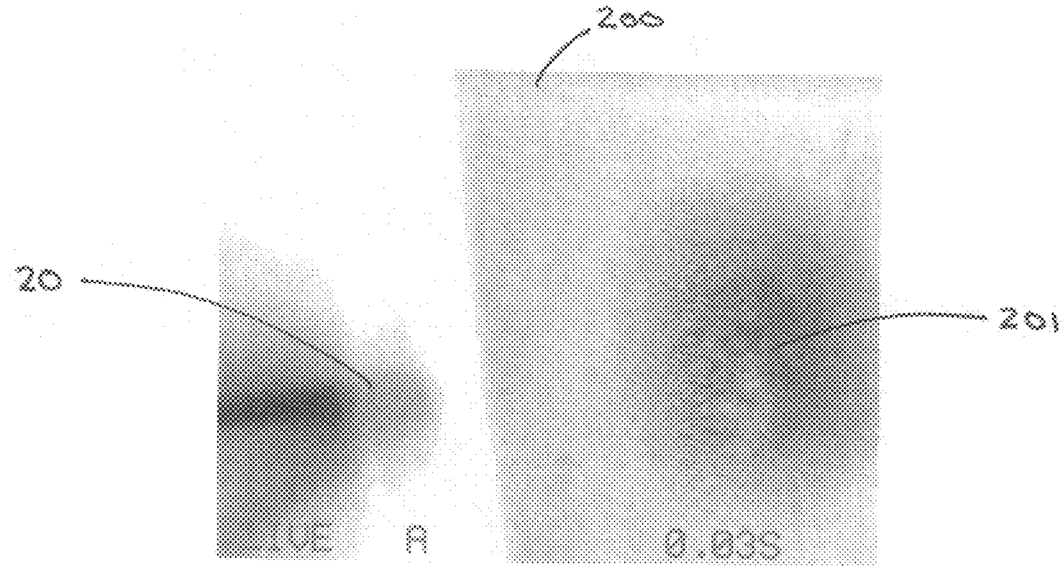
FIG. 7A shows a sample ferrofluid having nano-sized M particles organized in response to the field produced by the probe.
Figure 7B:
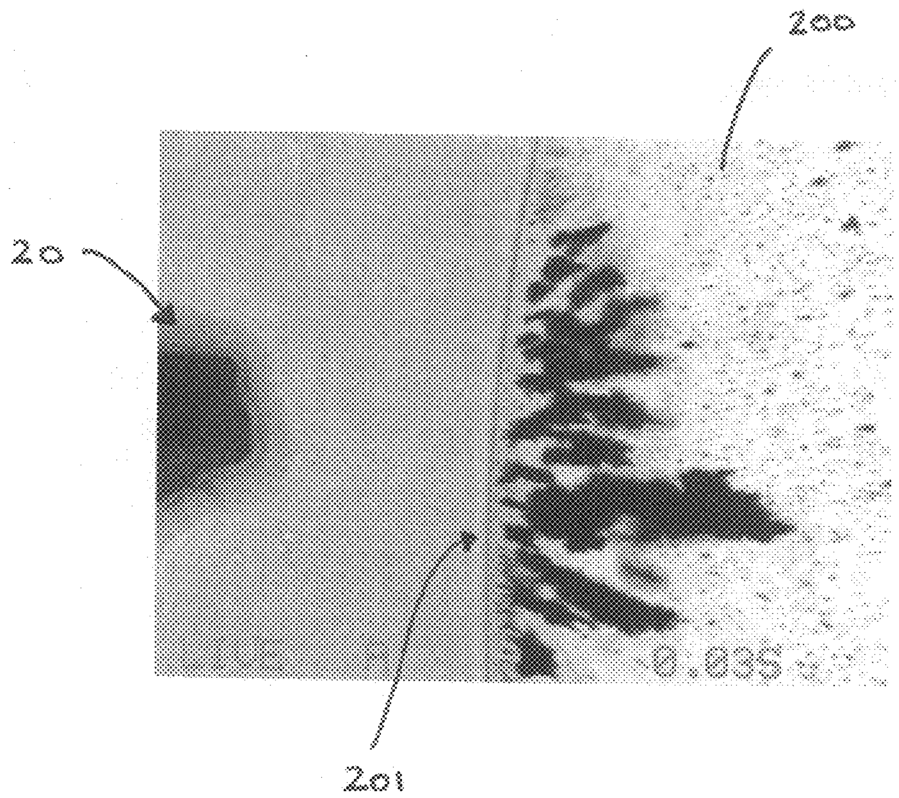
FIG. 7B shows a sample ferrofluid having micro-sized M particles organized in response to the field produced by the probe.

The stylus probe can also be handheld for use with a microscope, but such is not preferred. The micromanipulator mounted probe allows the user to precisely position the probe tip with respect to an in vitro sample containing a ferrofluid. By controlling the position of the probe tip and the magnitude of the electromagnet field, the user can control or steer the movement of the magnetic labeled particles, molecules, liquids, or cells (i.e. the "M particles") in a ferrofluid to a desired position. When the probe is positioned on a microscope, the user can visualize the probe tip and ferrofluid sample and view the movement of the M particles (assuming the particles are of sufficient size to be viewable through the microscope) to assist in steering the M particles to a desired location, such as is shown in FIG. 7. FIG. 7A shows the probe tip 20 placed next to a liquid sample containing nanometer sized paramagnetic M particles. Shown in the droplet 200 are the paramagnetic particles organized in a region 201 near the probe tip. FIG. 7B shows a similar result, but the M particles are larger and are coated with a drug.

The electromagnetic probe can be used to separate or concentrate the magnetic labeled particles in a ferrofluid at or on a desired location. For instance, it may be desired to concentrate the M particles in an in vitro sample onto a structure. The structure is placed in the sample and the electromagnet probe positioned behind the structure where the M-particles are desired to be located. The probe is activated drawing the M particles toward the desired structure location. After the desired concentration of M particles onto adjacent the structure is achieved, the coated structure can be removed. The probe tip is placed near the ferrofluid sample and may be placed within the ferrofluid sample, but is generally not preferred. If the probe is located in the fluid, magnetic particles may become attached to the probe surface contaminating the probe tip. However, such a placement does allow for efficient separation of the M particles despite probe contamination. Upon elimination of electrical power, the probe may retain a degree of magnetization (residual magnetism) making removal of probe attached M particles difficult. This memory magnetization can be reduced by choice of material construction for the probe, such as using low magnetic memory materials, such as soft iron or super paramagnetic materials. Alternatively demagnetization of the probe may be accomplished by subjecting the probe to a succession of magnetic forces which alternates in direction and gradually diminished in strength from a high value to zero. This process can be carried out in a few seconds and the probe metal can be brought to a condition which closely approximates loss of magnetism.

The electromagnetic probe can be used in a variety of procedures in conjunction with ferrofluids. For instance, as mentioned above, the probe can be used to separate/concentrate M particles and to deliver or steer and position M particles to a desired location on a surface or in a given volume. Such techniques are useful for directly separating or concentrating M particles for later use, or for guiding M particles onto or near a structure for later use. Additionally, a series of electromagnet probes can be utilized in conjunction with a ferrofluid to gently stir or mix the fluid. By placing a series of probes around the sample and pulsing (energizing or activating the power for a period of time) the probes in a pattern or sequence, the M-particles within the sample will act as miniature agitators and accomplish the mixing function. For example, two probes can be located on opposite sides of the sample (or three probes positioned 120 degrees apart, etc.) and pulsed in sequence to move the M particles. The length of the pulse will depend upon the size and mass of the M particles to be moved. After sufficient mixing has taken place, the M particles can be removed (if desired) by directing such to a designated removal location through the use of one of the series of probes. Gentle stirring or mixing can be accomplished in small samples without the need for a blade agitator commonly used in prior art magnetic mixing techniques, such as shown in U.S. Pat. No. 4,090,263 or 6,382,827 (using a ball agitator). This technique will generally be useful for small samples.

Alternatively, the probe can be utilized to separate out biomolecules or cellular material that has been exposed to and has incorporated M particles. For instance, biomolecules useful in cellular interactions or cellular metabolism that have been labeled or associated with M-particles can be used to monitor cell functions. Cells can be exposed to the labeled biomolecules for a period of time, and the cellular medium later washed to remove unused labeled Biomolecules (for instance, Biomolecules that have not be metabolized). The cells incorporating the labeled biomolecules can then be separated using the electromagnetic probe, allowing quantification of internal cell functions and/or cellular metabolism rates.

Further, a researcher who wants to understand the function of a particular type of cell must first separate that cell from other cells in a mixture. Several physical, chemical, and biological means can achieve separation, but antibodies suit this application well because of their great diversity and specificity. The process starts by associating an antibody specific for a particular target type of cell with M particles (such as through covalent bonding). The cells are incubated in a solution with the magnetically labeled antibodies and separated using the electromagnetic probe with a magnetic field strength as needed to effectively collect the labeled cellular material.

Additionally, the electromagnetic probe can be used to deliver M-particle labeled biomolecules to sites to enhance the ability of researchers to study cellular interactions, For instance, M-particles can be used to label a drug or encapsulated drug. The drug can be effectively directed to cell locations (using a microscope to visualize placement) for study or application by using the electromagnetic probe to steer the encapsulated or labeled drug to the desired site.

Figure 8:
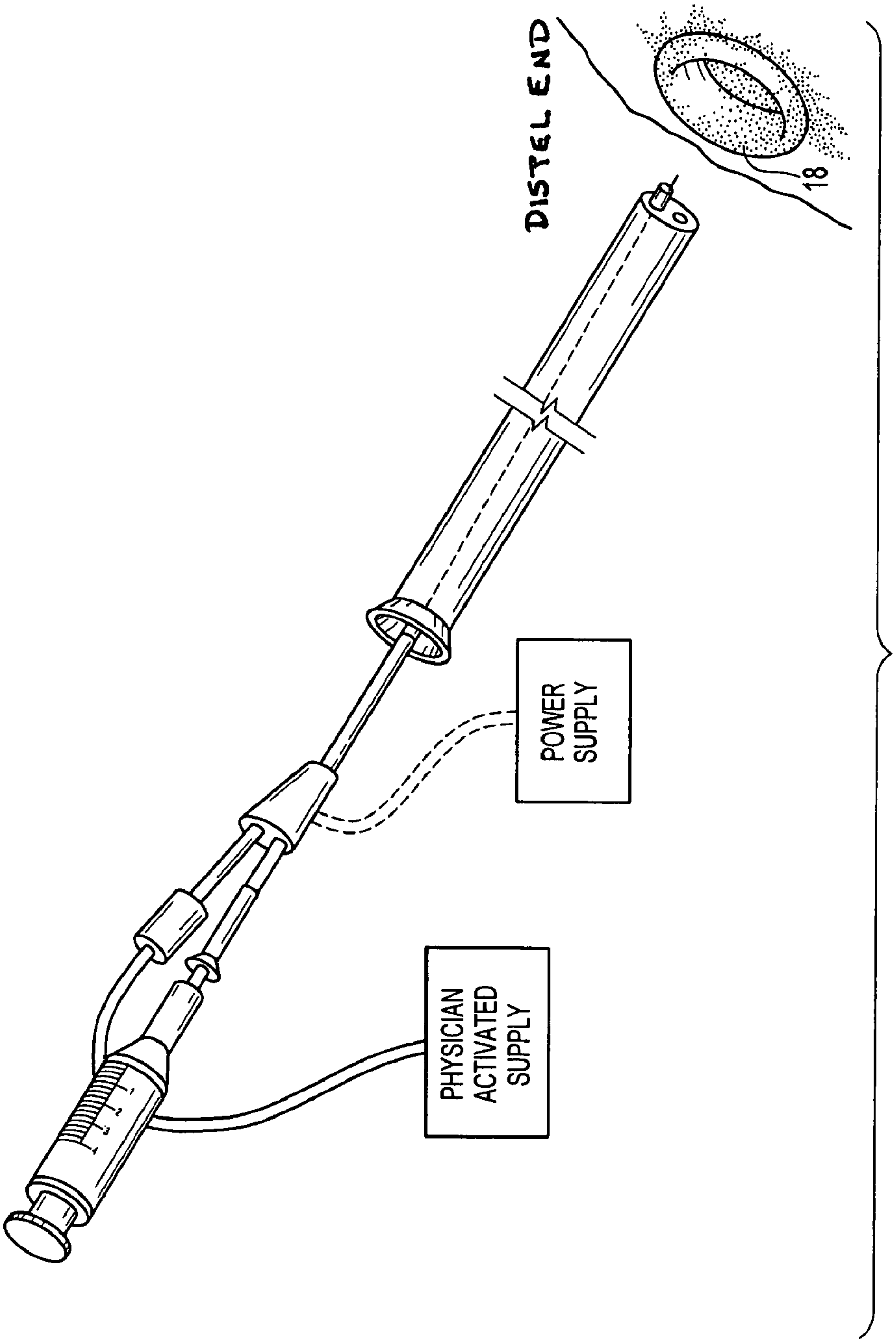
FIG. 8 shows a prior art catheter that can be modified to carry an electromagnetic probe.

However, drug or biomolecule delivery can additionally be accomplished with the probe in an in vivo environment. The device can be incorporated into a modified endoscope or catheter for use in vivo. For instance, shown in FIG. 8 is a catheter having a retractable needle placed on its distal tip (opposite the operator end, that end intended to remain outside the body), as described in U.S. Pat. No. 5,261,889 (hereby incorporated by reference). The needle tip of this device can be replaced with a scaled down electromagnetic probe where the wires to power the probe can be disposed within the lumen containing the electromagnetic probe (as indicated by 40 in FIG. 9). In such a modification, the core of the probe would be retractable within the lumen. The windings may be fixed in the lumen and the core retractable through the windings or the windings may be retractable in the lumen with the core. However, the probe could simply be mounted or incorporated into the distal end of the catheter if retraction was not a desired or required function. The electromagnetic probe in this device could have a hollow core to allow fluids to be injected at a desired location through the probe, or the catheter could be equipped with an additional separate lumen for drug injection or a separate catheter could be used for drug delivery or injection.

Figure 9:
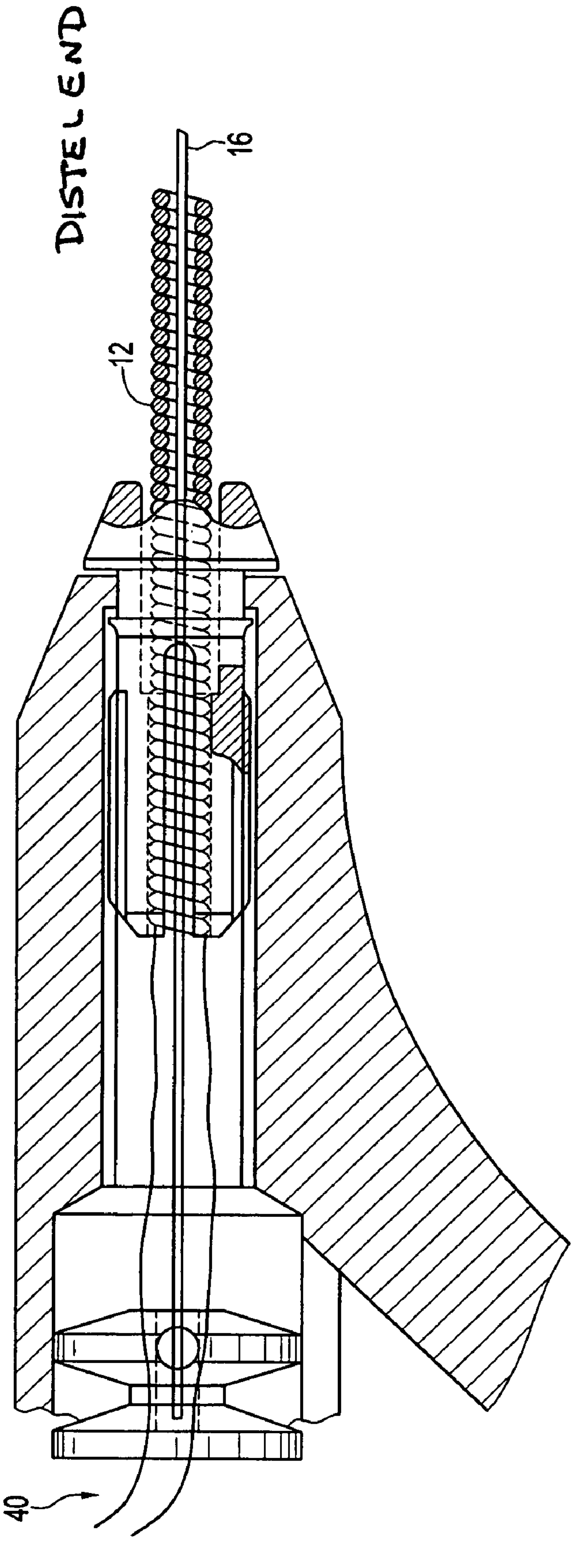
FIG. 9 shows a prior art endoscope that can be modified to carry an electromagnetic probe.

The electromagnetic probe can also be placed on the end of an endoscope. For instance, the endoscope shown in U.S. Pat. No. 5,632,764 (incorporated by reference), a portion of which is shown in FIG. 9, depicts an endoscope having a center core 16 with spring windings 12 around the center core. A forceps is positioned on the distal end of the core. This device can be easily modified into an electromagnet probe by removing the forceps, constructing the core from suitable materials and supplying power to the windings through the lumen in the handle of the endoscope. In this device, the core runs the length of the device. It may be desired to restrict the magnetic field effects to the distal end of the core, and hence, only the distal tip of the core need be constructed of magnetizable material. In use, to protect the in vivo environment, it may be desired to sheath the core, much as in a catheter type embodiment. Additionally, the sheath may be constructed of or have a lining of a shield material to prevent leakage of the magnetic field in areas away from the probe tip. For instance, a ferrous alloy sheath can be used to focus the field lines into the sheath, reducing magnetic radiation away from the sheath. The modified endoscope as described above may be incorporated into an endoscope having a lumen for drug delivery, as shown in U.S. Pat. No. 5,429,596 (hereby incorporated by reference) or U.S. Pat. No. 6,309,375 (hereby incorporated by reference).

As an example of use, the electromagnetic probe/endoscope or a catheter combination described above can be used to administer therapeutic agents (such as chemotherapeutic materials) to a tumor. The therapeutic materials are labeled or associated with a magnetic material (such as nano-encapsulated chemotherapy solutions where the nano-capsule has incorporated M particles) and are delivered through the endoscope near or adjacent to the tumor. The injected fluids can then be steered through the endoscope mounted electromagnet probe to various locations on the tumor by suitable placement of the probe tip. For instance, if the drugs are dispensed near an anterior surface of a tumor; the probe can be positioned on the posterior surface of the tumor, and activated. The magnetic field will extend through the tumor and the labeled drug would then be drawn onto the tumor surface for adsorption. After a suitable period of time, the probe would be deactivated and removed. The ability to attract the M particles through a tumor will decrease with tumor thickness. If a bendable or flexible tip is desired, the core of the probe can itself be coiled to allow flexibility. Alternatively, the solid core can be dispensed with, but the field induce with an "air" core will not be as strong as that from a paramagnetic material.

The probe, in conjunction with M particles labeled cells, can also be used to study cell morphology, cell differentiation, and cell stress. For instance, it is known that application of mechanical loads to osteoblasts regulates skeletal mass. (see "In Vitro effects of Dynamic Strain on the Proliferation and Metabolic activity of Human Osteoblasts," Kaspar et al, *J. Musculoskeletal Neuronal Interaction*, December 2000; "Physiological Strains Induce Differentiation on in Human Osteoblasts Cultured on Orthopedic Biomaterials" Di Palma et al, *Biomaterials*, August 2003. Cells can be placed under stress by having M particles incorporated into the cellular materials and the cells exposed to the field generated by one or more electromagnetic probes. The stress induces stretching of the cell due to the movement of the incorporated magnetic particles within the field produced by the electromagnetic probe. By movement of the probe (or varying the intensity of the field), the cellular reaction to induced differential stretching can be observed, allowing for a researcher to control the type and degree of stretching.

Other uses and embodiments of the invention will occur to those skilled in the art, and are intended to be included within the scope and spirit of the following claims.

We claim:

1. A system, comprising: an electromagnetic probe, a ferrofluid containing particles, and an arrangement configured to simultaneously view the probe tip and the movement of the particles, the particles including material that is responsive to a magnetic field, the electromagnetic probe positioned near said ferrofluid and configured to steer the particles in the ferrofluid.

2. The system of claim 1, wherein said electromagnetic probe is a DC driven electromagnetic probe.

3. The system of claim 1, wherein said electromagnetic probe further comprises a stylus magnetic probe.

4. The system of claim 3, further including a micromanipulator, the micromanipulator configured to carry the stylus electromagnetic probe.

5. The system of claim 1, wherein the electromagnetic probe includes conductive windings and a pointed end, the pointed end configured to channel a magnetic field generated by the conductive windings around an axis of the pointed end, the magnetic field generated around the pointed end such the particles in the ferrofluid are steerable without contacting the electromagnetic probe.

6. The system of claim 5, wherein the electromagnetic probe is configured to steer the particles to a desired location on at least one of a surface and a volume.

7. The system of claim 1, wherein the electromagnetic probe is comprised of at least one of a soft iron and a super paramagnetic material.

8. The system of claim 1, wherein the arrangement includes at least one of a microscope and an endoscope.

9. A method of steering particles contained in a ferrofluid, comprising: positioning an electromagnetic probe near a ferrofluid sample; activating said electromagnetic probe for a period of time, the particles including material that is responsive to a magnetic field; and using an arrangement configured to simultaneously visualize the electromagnetic probe tip and the ferrofluid to assist in steering the particles to a desired location.

10. The method of claim 9, wherein the electromagnetic probe includes conductive windings and a pointed end, the pointed end configured to channel a magnetic field generated by the conductive windings around an axis of the pointed end.

11. The method of claim 9, wherein the arrangement includes at least one of a microscope and an endoscope.

12. A method of separating a constituent from a flowable sample, comprising: associating particles with a flowable sample or a constituent of the flowable sample, the particles including material that is responsive to a magnetic field; providing an electromagnetic probe and operating said electromagnetic probe to steer the particle associated constituent to a desired position; isolating the particle associated constituent from the flowable sample, wherein the electromagnetic probe does not contact the flowable sample; and using an arrangement configured to simultaneously visualize the electromagnetic probe tip and the ferrofluid to assist in steering the particles to a desired location.

13. The method of claim 12, wherein the arrangement includes at least one of a microscope and an endoscope.

* * * * *